(12) United States Patent
Giessler et al.

(10) Patent No.: US 10,964,022 B2
(45) Date of Patent: Mar. 30, 2021

(54) IMAGE PROCESSING METHOD, CORRESPONDING IMAGE PROCESSING APPARATUS AND ENDOSCOPE ARRANGEMENT

(71) Applicant: Scholly Fiberoptic GmbH, Denzlingen (DE)

(72) Inventors: Nicole Giessler, Triberg (DE); Sebastien Weitbruch, Niedereschbach (DE)

(73) Assignee: SCHOLLY FIBEROPTIC GMBH, Denzlingen (DE)

( * ) Notice: Subject to any disclaimer, the term of this patent is extended or adjusted under 35 U.S.C. 154(b) by 1155 days.

(21) Appl. No.: 14/953,919

(22) Filed: Nov. 30, 2015

(65) Prior Publication Data

US 2016/0189363 A1  Jun. 30, 2016

(30) Foreign Application Priority Data

Dec. 30, 2014 (DE) .......................... 102014019584.8

(51) Int. Cl.
| | |
|---|---|
| *G06T 7/11* | (2017.01) |
| *A61B 1/00* | (2006.01) |
| *G06K 9/00* | (2006.01) |
| *G06K 9/34* | (2006.01) |
| *G06T 7/194* | (2017.01) |
| *G06K 9/38* | (2006.01) |

(52) U.S. Cl.
CPC ............ *G06T 7/11* (2017.01); *A61B 1/00009* (2013.01); *G06K 9/00496* (2013.01); *G06K 9/00523* (2013.01); *G06K 9/342* (2013.01); *G06K 9/38* (2013.01); *G06T 7/194* (2017.01)

(58) Field of Classification Search
None
See application file for complete search history.

(56) References Cited

U.S. PATENT DOCUMENTS

| | | | | |
|---|---|---|---|---|
| 2004/0001195 A1* | 1/2004 | Ge | ......................... | G06T 7/136 |
| | | | | 356/73.1 |
| 2004/0071342 A1* | 4/2004 | Locht | ....................... | G06T 7/11 |
| | | | | 382/164 |

OTHER PUBLICATIONS

S.M. Smith & J.M. Brady, "SUSAN—A New Approach to Low Level Image Processing", 23 Int'l J. of Comp. Vision 45-78 (1997) (Year: 1997).*
S. Lazebnik, C. Schmid, & J. Ponce, "A Sparse Texture Representation Using Affine-Invariant Regions", 2 Proc. of the 2003 IEEE Comp. Soc'y Conf. on Comp. Vision & Pattern Recognition 319-324 (Jul. 2003) (Year: 2003).*
C. Schmid, R. Mohr, & C. Bauckhage, "Evaluation of Interest Point Detectors", 37 Int'l J. of Comp. Vision 151-172 (2000) (Year: 2000).*

* cited by examiner

*Primary Examiner* — David N Werner
(74) *Attorney, Agent, or Firm* — Volpe Koenig

(57) ABSTRACT

In an image processing method (18), for images (9) in a image sequence (8), in each case a position indication (23) of a center (24) of the image content (10) of individual images (9) is calculated in a completely computer-implemented and/or hardware-implemented, statistical evaluation method (20). The center (24) is defined by a circle section (62) which is described or characterized by a separation line (12) between the image content (10) and a periphery (11) which is supplementary to the image content (10) in the image (9) or complementary therewith.

18 Claims, 4 Drawing Sheets

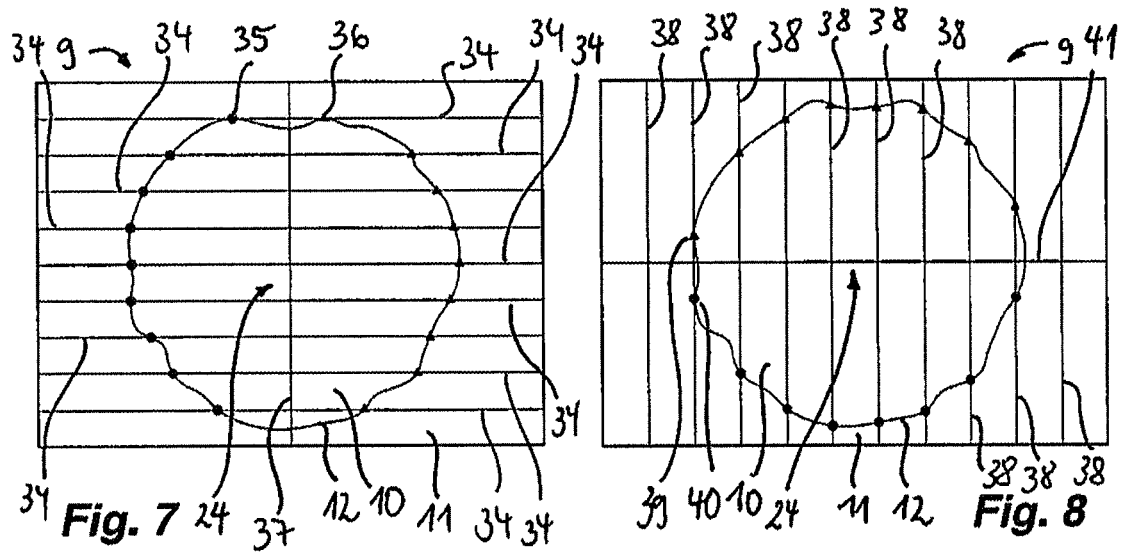
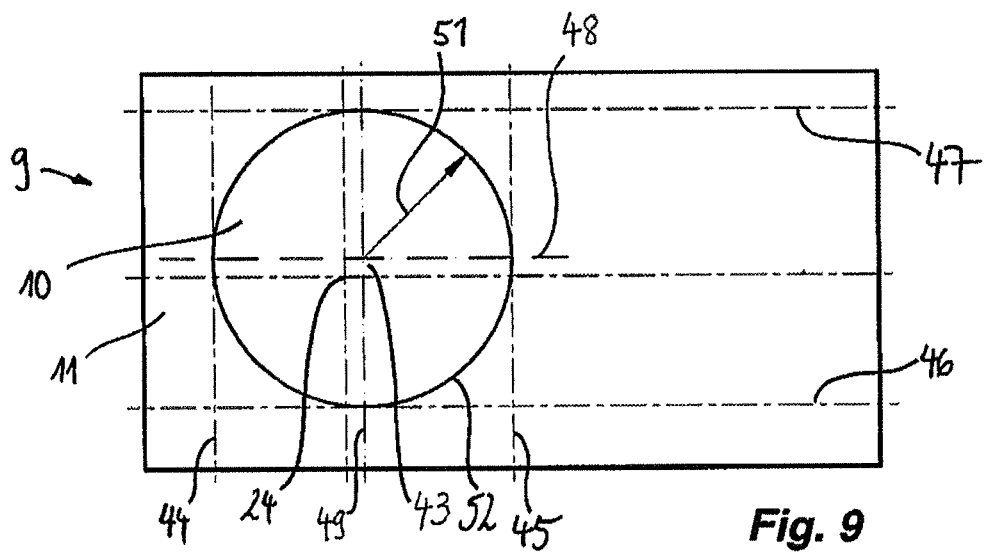
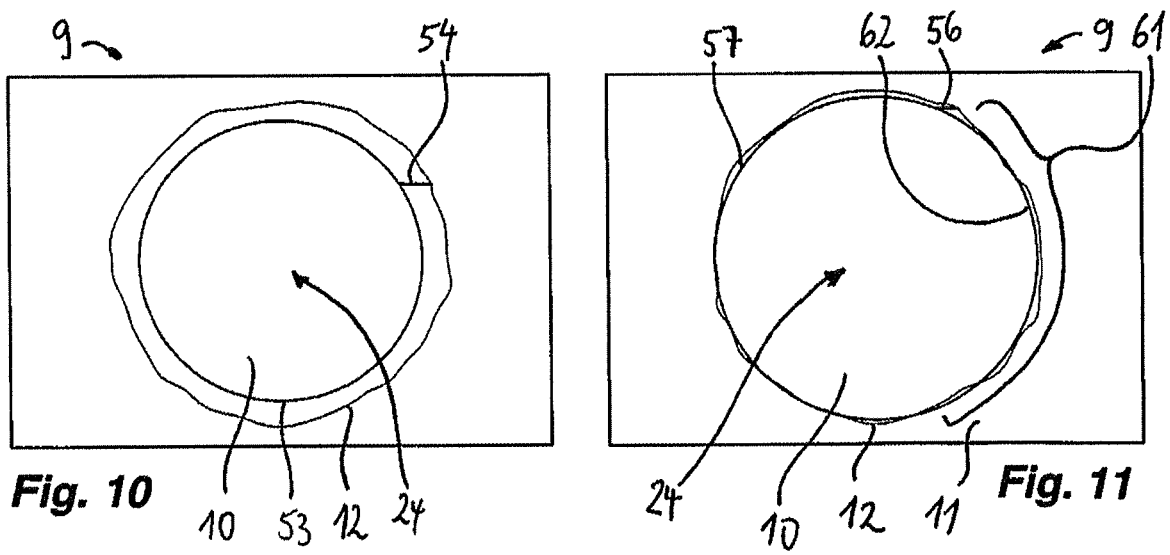

IMAGE PROCESSING METHOD, CORRESPONDING IMAGE PROCESSING APPARATUS AND ENDOSCOPE ARRANGEMENT

INCORPORATION BY REFERENCE

The following documents are incorporated herein by reference as if fully set forth: German Patent Application No.: 102014019584.8, filed Dec. 30, 2014.

BACKGROUND

The invention relates to an image processing method, wherein an image sequence of images is processed which in each case have an image content and a periphery that is complementary to the image content, wherein the image content is separated from the periphery by a separation line that describes in at least one section a circle section.

Such image sequences are known for example from the use of endoscopes with digital image capturing devices, wherein the circle section is given by an edge of an optical unit for image recording, while an extent of the entire image is prespecified by a dimension of an image recording chip. In this way, images are produced which are divided by a separation line into an image content and a periphery which is to be represented generally in black or otherwise without content.

The used image capturing devices frequently have an adjustable optical unit that is connected upstream, by way of which a focusing function and/or a zoom function are realizable. The image content fills the image to varying extents in dependence on the setting of the adjustable optical unit. The filling of the image can also differ if an optical unit of the endoscope is interchanged, as is the case for example in endo-couplers (endoscopic couplers).

The invention furthermore relates to an image processing apparatus having an input via which a sequence of images can be input, which have in each case an image content and a periphery that is complementary to the image content, wherein the image content is separated from the periphery by a separation line which describes in at least one section a circle section, and having an output, via which for each image a position indication of a center of the image content that is defined by the circle section can be output.

The invention finally relates to an endoscope arrangement having an endoscope and an image capturing device.

SUMMARY

The invention is based on the object of improving the representation of an image sequence recorded with an endoscope arrangement.

To achieve this object, the invention provides an image processing method including one or more features of the invention as described below. In particular, an image processing method of the type described in the introductory part is provided to achieve the stated object according to the invention that for each image of the image sequence, a position indication of a center of the image content that is defined by the circle section is ascertained in a computer-implemented and/or hardware-implemented, statistical evaluation method. In the invention, it is generally possible for the computer implementation to be effected by way of appropriate programming and/or for the hardware implementation to be effected, for example, by way of a hardware description language such as VHDL and/or in an FPGA. The invention has the advantage that increased robustness can be achieved when ascertaining the defined center of the image content due to the use of a statistical evaluation method. This is because it has been found that the above-mentioned separation line in the individual images describes a section of a circle section, while not completely extending on this circle section. The reason for this can be reflections within the endoscope before the image recording and/or dark regions in the recorded image content, for example on account of poorly lit objects in a hollow space. A typical separation line therefore has deviations from the circle section, which can vary from image to image in the image sequence, for example because a user moves the endoscope and/or because the recorded object has moved. Due to the use of the statistical evaluation method, a balancing effect is achieved here, which frequently avoids large jumps of the ascertained position indications from image to image.

It is particularly expedient if the separation line in the images of the image sequence describes in each case one complete circle, such that the image content is in each case distanced on all sides from a boundary of the image by the periphery. The description of a circle or a circle section by the separation line can generally be characterized by the circle or the circle section forming an approximation or smoothing of the separation line.

In one configuration of the invention, provision may be made for in each case a value for a component of the position indication to be calculated for a selection of rows from positions of intersection points of the row with the separation line in the statistical evaluation method. Advantageous is here that it is possible to ascertain row-wise in each case a maximum extent of the image content for the selection of rows. Therefore the value can be calculated by averaging. It has been shown that usable values for the statistical evaluation method can be obtained in this way.

Alternatively or additionally, provision may be made for in each case a value for a component of the position indication to be calculated for a selection of columns from positions of intersection points of the column with the separation line in the statistical evaluation method. It is advantageous here that a second component of the position indication can be calculated. Here, too, it is particularly expedient if the value that is calculated in column-wise fashion is calculated in each case by averaging from the associated positions of the intersection points.

Is particularly expedient here if only those rows or columns are selected that are intersected by the circle section at two intersection points. This is particularly expedient if the image content does not describe a complete circle, but the associated circle form intersects an edge of the image at least in one direction.

In one configuration of the invention, provision may be made for a frequency distribution of the values that are calculated for the selection of rows or columns to be calculated in the statistical evaluation method. The calculation of a frequency distribution has proven to be a useful means for achieving a particularly high robustness against fluctuations in the image contents and/or peripheries between the images.

It is particularly expedient here if, for ascertaining the position indication, the in each case most frequent calculated value for the selection of rows or columns is used. What can be achieved in this way is that outliers in individual rows or columns, which result for example from unintended temporary darkening in the image content and/or temporary reflections in the periphery, can be suppressed particularly well.

In one configuration of the invention, provision may be made for an intensity and/or color value histogram to be calculated in computer-implemented and/or hardware-implemented fashion for the respective image before the statistical evaluation method. It is advantageous here that a means is available for identifying the respective periphery of the respective image in a computer-implemented and/or hardware-implemented fashion. This is because it has been found that the peripheries in the recorded images are characterized by substantially black pixel values, while the image contents have intensity and/or color values that deviate from a black coloration.

It is particularly expedient here if the images are subject to filtering, for example in a filtering step, before the calculation of the intensity and/or color value histogram. In this way, bright image pixels which were produced through noise or in another way can be suppressed. A homogenous capturing of the periphery can thus be achieved.

Provision can be made, for example, for all image pixels of an image, the intensity and/or color value of which lies under a threshold value, to be colored black. It is advantageous here that a homogenous periphery can be generated which can be processed particularly well in the statistical evaluation method.

In one configuration of the invention, provision may be made for the threshold value for an image segment in which the respective image pixel is located to be individually prespecified and/or ascertained. To this end, provision can be made for the current image to be segmented or divided into image segments. This can be done in an image segmenting and histogram calculation step. The invention here uses the knowledge that identical treatment of all image pixels of the periphery is unfavorable if local reflections occur, for example, in a recording endoscope. It has been shown that such reflections are local, with the result that it is expedient for an image to be divided into image segments for which in each case an individual threshold value is used that can be obtained from the respective intensity and/or color value histogram for this image segment. It is particularly expedient here if the image segment is defined by two straight lines which intersect in the image. It is possible in this way for reflections in the peripheries which extend typically like beams from a center to be eliminated particularly well.

In one configuration of the invention, provision may be made for the threshold value to be calculated from the intensity and/or color value histogram. This can be provided for example by an intensity and/or color value which defines a minimum in the intensity and/or color value histogram. Thus automatic adaptation of the threshold value is possible.

In order to further improve the results of the statistical evaluation method, provision may be made for an edge detection method to be applied before the statistical evaluation method for the respective image. What is advantageous here is that the separation line can thus be enhanced, with the result that the already mentioned values, for example, can be determined with more accuracy.

In one configuration of the invention, provision may be made for a second position indication for the center to be calculated as an average of a maximum extent and a minimum extent of the image content in the row direction and in the column direction for each image. What is advantageous here is that a second variable is provided for a plausibility check of the calculated position indication, which in this case can be referred to as a first position indication.

Provision may be made, for example, for the first position indication to be discarded and/or for the position indication relating to a preceding image in the image sequence to be kept if it deviates too strongly from the second position indication. It is thus readily possible to identify when the statistical evaluation method has supplied unreliable values for the position indication because of a particular recording situation or for other reasons. Alternatively, provision may be made to wait for or record further images if a deviation between the first position indication and the second position indication is too strong in order to obtain more accurate results.

In one configuration of the invention, provision may be made for a radius of the circle section to be calculated for each image. What is advantageous here is that modelling of the separation line by way of an exact circle is made possible.

It is particularly expedient here if the radius is calculated from a maximum extent and a minimum extent of the image content in the row direction and/or in the column direction, in particular from the already mentioned maximum extent and the already mentioned minimum extent.

This way enables a simple method for calculating the radius. The radius can here be calculated, for example, as half the diameter given by the maximum extent and the minimum extent.

In one configuration of the invention, provision may be made to calculate a deviation of the separation line from a circle which is defined by the position indication and by a radius, in particular the radius that has already been mentioned, along the section. What is advantageous here is that an assessment variable for assessing a quality of the statistical evaluation method for the respective images can be provided.

Provision may be made, for example, to calculate a second deviation of the separation line from a circle which is defined by the position indication and the radius, which were calculated for a preceding image in the image sequence, along the section. What is advantageous here is that a comparison variable can be provided with which fluctuations of unintended strength of the radii and the position indications, which are continuously calculated in each case for the images, are available. The previously mentioned deviation can here be referred to as a first deviation.

The mentioned deviations can be calculated, for example, by integration by error squared or in other ways. It is particularly expedient here if the position indication (calculated for the respectively current image) is discarded and/or the position indication for a preceding image in the image sequence is kept if the (first) deviation is greater than the second deviation. In this way it is possible to avoid the calculated values jumping or drifting randomly due to unfavorable recording conditions.

Provision can be made here for the position indication that is calculated for a current image and the associated radius to be replaced by a value pair with respect to the preceding image.

In one configuration of the invention, provision may be made for at least one image editing step to be carried out for each image, which image editing step processes at least the position indication as a parameter. What is advantageous here is that an image editing step can be carried out which takes into account a size and/or a position of the image content in the image.

Provision may be made here, for example, for the image editing step to be a matching of an enlargement such that the respective image content fills the available image format and/or is a centering of the respective image content. What is advantageous here is that it is possible to achieve good utilization of an output format, which is available at an output unit.

In one configuration of the invention, provision may be made for further image editing steps to be additionally carried out, for example a white balance, contrast equalization, tonal correction, histogram matching and/or setting of an associated optimum exposure time. What is advantageous here is that such image processing steps frequently benefit from an arrangement of the actual image content that fills the space to the greatest possible extent. Furthermore advantageous is that the further image editing steps can be related to the real image content, while any influence of the periphery can be suppressed or at least reduced.

To achieve the stated object, the features of the coordinate claim that is directed to an image processing apparatus are provided according to the invention in an image processing apparatus. In an image processing apparatus of the type described in the introductory part, it is thus in particular proposed for achieving the stated object that a processing device is configured and adapted for carrying out an image processing method according to the invention, in particular as previously described and/or as claimed in one of the claims that are directed to an image processing method. What is advantageous here is that a compact processing apparatus can be provided, which can be operated for example with an endoscope.

It is particularly expedient here if the processing device is realized in an FPGA (field programmable gate array). Advantageous is here that a cost-effective image processing apparatus can be provided.

Alternatively or additionally, provision may be made for an output unit to be adapted to output processed images. What is advantageous here is that a result of the image processing method according to the invention for the individual images can be output in real time and/or synchronously with the recording of new images in the image sequence. The processed images can here be subjected to the at least one image processing step already mentioned and/or can contain the position indication and/or the radius of the parameter.

In order to achieve the stated object, provision is made according to the invention in the endoscope arrangement of the type described in the introductory part for an image processing apparatus according to the invention to be configured in particular as previously described and/or as claimed in one of the claims for protection that are directed to an image processing apparatus. What is advantageous here is that an endoscope arrangement is provided, in which the advantages of the image processing method according to the invention can be realized.

BRIEF DESCRIPTION OF THE DRAWINGS

The invention will now be explained in more detail with reference to exemplary embodiments, but is not limited to the exemplary embodiments. Further exemplary embodiments can be gathered from a combination of the features of individual or multiple claims for protection with one another and/or with individual or multiple exemplary embodiments.

In the figures:

FIG. 7 illustrates the calculation of a value for a horizontal component of the position indication, FIG. 8 illustrates the calculation of a value for a vertical component of the position indication in a method according to the invention, FIG. 9 illustrates the calculation of a second position indication and a radius in an image processing method according to the invention, FIG. 10 illustrates the calculation of a deviation of a separation line from a circle that is defined by the position indication and the radius, and FIG. 11 illustrates the calculation of a second deviation of the separation line of an image from a circle that is defined by calculation values of a preceding image.

DETAILED DESCRIPTION OF THE PREFERRED EMBODIMENTS

Figure 1:
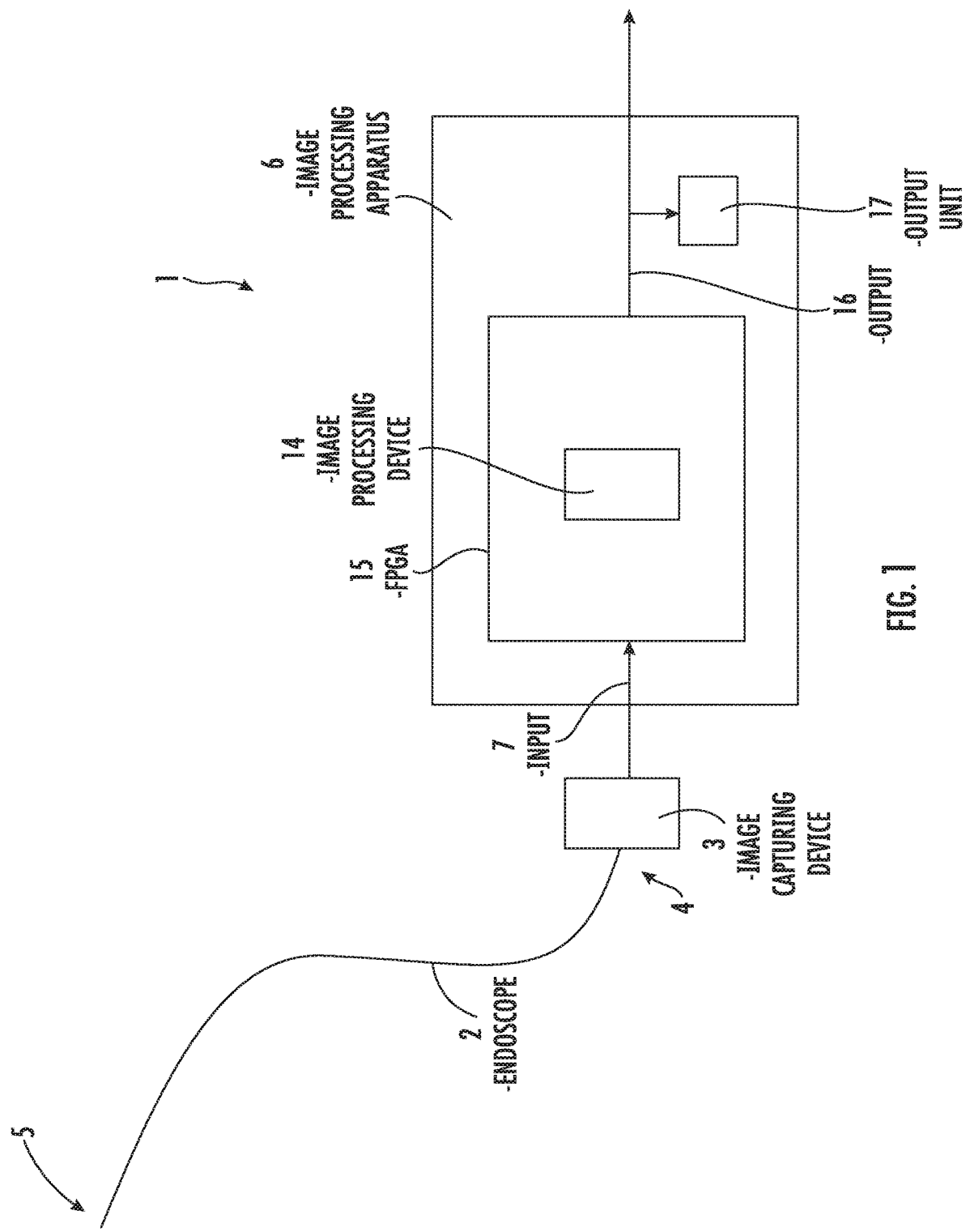
FIG. 1 illustrates in schematic representation an endoscope arrangement according to the invention having an image processing apparatus according to the invention.

An endoscope arrangement designated in FIG. 1 as 1 overall has an endoscope 2 and an image capturing device 3 in a manner known per se. The endoscope 2 is here illustrated as a flexible endoscope, but can also be configured as a rigid endoscope in another exemplary embodiment.

The image capturing device 3 is arranged in FIG. 1 at a proximal end 4 of the endoscope 2. In further exemplary embodiments, the image capturing device 3 can also be arranged directly at a distal end 5, such that the endoscope 2 in this case does not need to have any optical conductor. The image capturing device 3 is preferably configured as a digital image capturing device with an image recording chip and supplies an image sequence 8 of images 9 (illustrated in FIG. 3 by way of example) to the image processing apparatus, designated as 6 overall, via an input 7. The images 9 have in each case an image content 10 which completely or at least partially images a field of view of the endoscope 2 and a periphery 11 that is in each case complementary thereto in the image 9. The image 9 is composed therefore of in each case an image content 10 and a periphery 11, which are separated from one another by a separation line 12.

Figure 3:
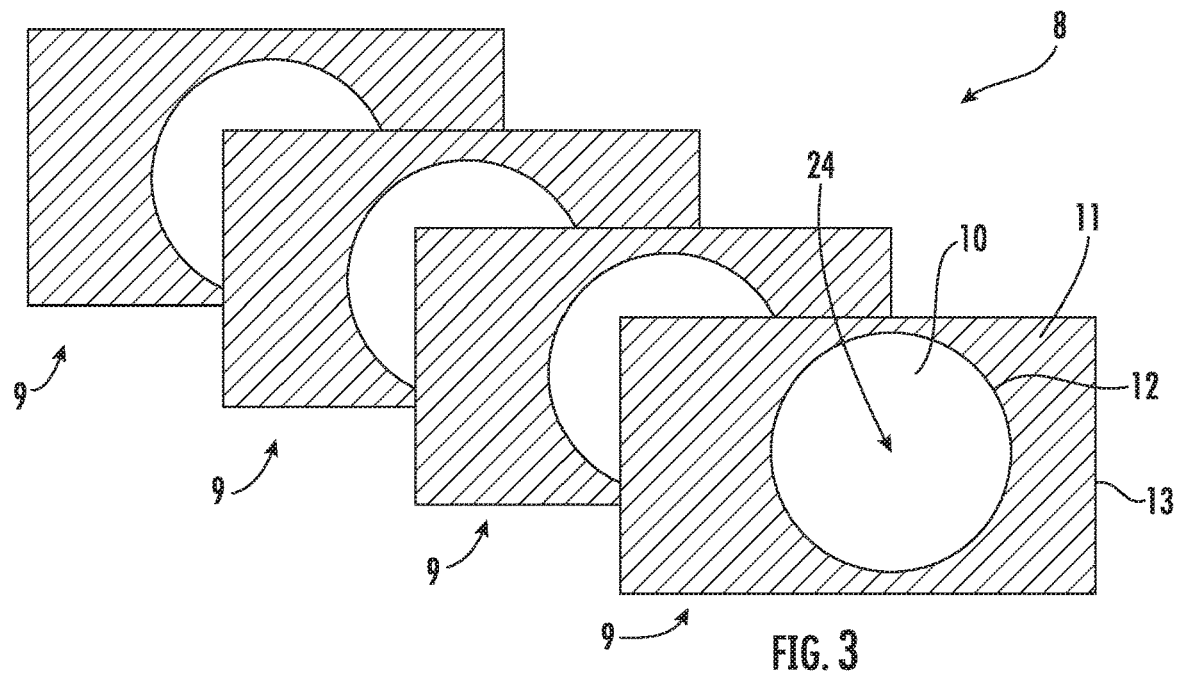
FIG. 3 illustrates in highly simplified representation an image sequence of images with in each case an image content, a separation line and a periphery.

The separation line 12 defines in a section 61 (cf. FIG. 11) in each case a circle section 62, which in the case of FIG. 3 is even a full circle, but which, in the case where the separation line 12 intersects an edge 13 of the respective image 9 and therefore the full field of view is not completely contained in the respective image 9, is a circle section that is delimited by the edge 13.

FIG. 3 shows here a stylized representation, while for example FIGS. 7, 8, 10 and 11 show a more realistic representation of the separation lines 12.

Figure 2:
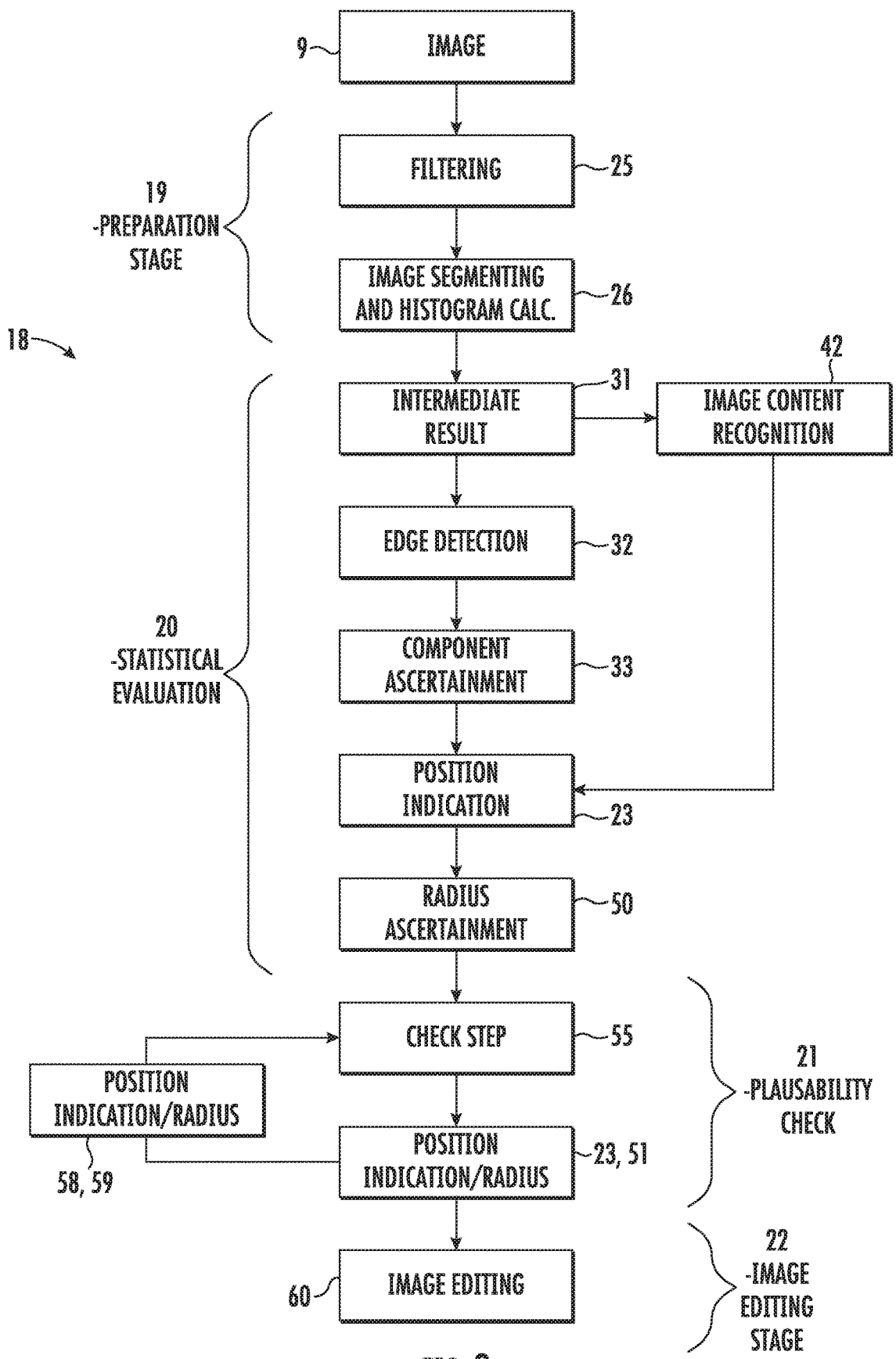
FIG. 2 illustrates a flow chart of an image processing method according to the invention.

Means 14 for carrying out an image processing method 18 according to the invention, which will be described in more detail below with respect to FIG. 2, are configured in the image processing apparatus 6, for example in the form of functional blocks of a software and/or in the form of a specific circuitry of logic gates.

In the exemplary embodiment addressed here, the means 14 are realized in an FPGA 15. For support purposes, in particular in more complex mathematical calculations, an embedded microcontroller can be present here.

The calculation results of the image processing method 18 according to the invention and the processed images 9 of the image sequence 8 can be output via an output 16 that is connected to an output unit 17, for example a monitor or another optical output unit, and/or to an external data memory and/or an external data processing device.

FIG. 2 shows by way of example a flowchart of an image processing method according to the invention that is designated overall as 18.

The image processing method 18 according to the invention takes an image 9 from the image sequence 8 according to FIG. 3 and processes it. The image processing method 18 can here be subdivided roughly into a preparation stage 19, a statistical evaluation method 20, a plausibility check stage 21 and an image editing stage 22. Other subdivisions are realized in further exemplary embodiments, or individual stages are carried out in a different order.

After the image processing method 18 is complete, it is carried out again for the next image 9 in the image sequence 8.

The statistical evaluation method 20 in the image processing method 18 according to the invention supplies here as the calculation result of the computer-implemented and/or hardware-implemented, fully automatic calculation for each input image 9 in the image sequence 8 a position indication 23 for the center 24 of the circle or circle section 62 that is described by the separation line 12 in each image 9. This center 24 at the same time forms the center of the respective image content 10.

In the preparation stage 19, the respective image 9 is first filtered in a filtering step 25 to increase in each case the homogeneity of the possibly noisy peripheries 11.

In an image segmenting and histogram calculation step 26, the current image 9 is subsequently divided into image segments 27 which are defined and separated from one another in each case by lines 28.

Figures 4, 5:
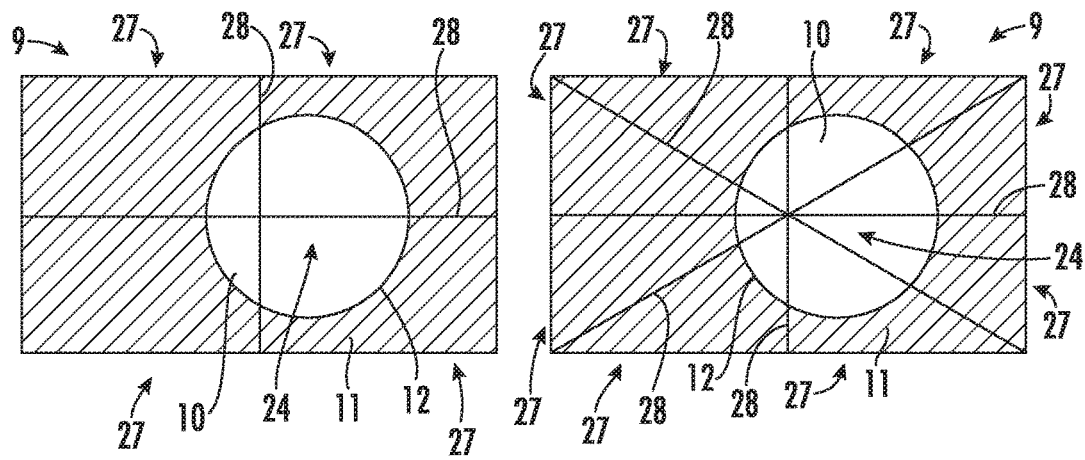
FIG. 4 illustrates a first segmenting of an image of the image sequence according to FIG. 3 into image segments in a method according to FIG. 2.
FIG. 5 illustrates a further segmenting of an image in the image sequence according to FIG. 3 into image segments in a method according to FIG. 2.

FIG. 4 here illustrates an image segmenting of an image 9 into four image segments 27 by way of two crossing lines 28. FIG. 5 illustrates an image segmenting of an image 9 into eight image segments 27 which are defined by four crossing lines 28.

Figure 6:
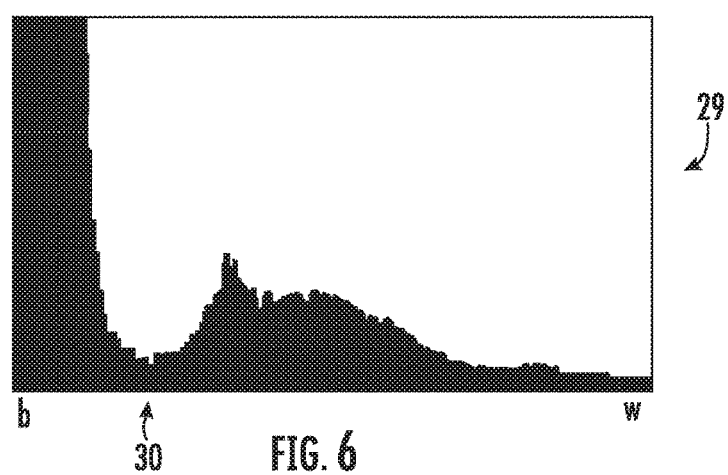
FIG. 6 illustrates an intensity and/or color value histogram with respect to an image in the image sequence according to FIG. 3.

For each of these image segments 27, subsequently an intensity and/or color value histogram 29, illustrated by way of example in FIG. 6, is calculated in a manner known per se.

On the x axis, the histogram 29 shows the intensity and/or color value, which can lie for example between a value "b" for black and a value "w" for white. Other color values can also be used. Plotted on the y-axis is the frequency with which the respective intensity and/or color value occurs in the image segment 27 or in the image 9.

Clearly recognizable in the intensity and/or color value histogram 29 is a threshold value 30, which separates the dark region of the periphery 11 from the comparatively light region of the image content 10. This threshold value 30 can be found for each image segment 27 in computer-implemented and/or hardware-implemented fashion for example by comparing a drop in the frequency distribution with plateaus which are given by the periphery 11 or the image content 10 to the left and right of the threshold value 30.

As a result, an intensity and/or color value histogram 29 has thus been obtained which is composed of different intensity and/or color value histograms for each image segment 27.

In the image 9, all image pixels, the intensity and/or color value of which lies under the threshold value 30, are then colored in a uniform black. This is carried out for each image segment 27 of the image 9 with an individually determined threshold value 30.

As a result, an image 9 is obtained in which the periphery 11 has a uniform intensity and/or color value black.

For this intermediate result 31, edge detection is carried out in an edge detection step 32 in order, in a manner known per se, to more clearly represent and to emphasize the separation line 12, which delimits the periphery 11, which is now uniformly colored, with respect to the image content 10.

In a component ascertainment step 33, according to FIG. 7, for each row 34 or a specified selection of rows 34, in each case the intersection points 35 and 36 of the row 34 with the separation line 12 are ascertained. For each row 34 that has been processed, a value for the horizontal component 37 of the position indication 23 is thus obtained as an average of the positions of the intersection points 35 and 36.

For these values, a frequency distribution across all (selected) rows 34 is established. The horizontal component of the position indication 23 is obtained as the most frequent value in the frequency distribution.

Likewise, for all or selected columns 38 according to FIG. 8 in each case the intersection points 39 and 40 of the respective column 38 with the separation line 12 are ascertained. For each (selected) column 38, a value for the vertical component 41 is then calculated as an average of the positions of the intersection points 39, 40 of the column. For these values, a frequency distribution over all (selected) columns 38 is established, and the vertical component 41 of the position indication 23 is obtained as the most frequent value in the frequency distribution.

After the component ascertainment step 33, the position indication 23 has thus been obtained.

In an alternative, a second position indication 43 according to FIG. 9 is ascertained in an image content recognition step 42 as follows. First, a minimum extent 44 and a maximum extent 45 of the image content 10 in the horizontal direction are ascertained. The horizontal component 48 is obtained as an average of the minimum (horizontal) extent 44 and the maximum (horizontal) extent 45 in the row direction. A vertical component 49 of the second position indication 43 is ascertained in a similar way. This is obtained as an average of the minimum (vertical) extent 46 and the maximum (vertical) extent 47 in the column direction.

In the image processing apparatus 6, a limit value is fixed which is compared to the difference between the first position indication 23 and the second position indication 43. If the difference exceeds the limit value in terms of amount, the first position indication 23 is discarded, or the first position indication 23 that was determined in relation to the preceding image 9 is kept. In this case, the more accurate position indication 23 does not deviate from the roughly approximated second position indication 43 so much that there could be doubt as to the quality of the statistical evaluation method 20. However, if the limit value is not exceeded, the position indication 23 is kept.

In a radius ascertainment step 50, according to FIG. 9, the radius of a circle 52 is then calculated as half the difference between the minimum extent 44 and the maximum extent 45. It has proven expedient here to carry out this calculation for the extents in the column direction if the images 9 are in the landscape format, and to use the extents in the column direction for the calculation if the images 9 are in the portrait format.

As a result, an image 9 has been obtained, in which the separation line 12 is represented in emphasized fashion, and which additionally contains a circle 53 (or a circle section 62 if the image content 10 is cut off by the edge 13), which is given by the radius 51 of the circle 52 and the position indication 23 as a center point or center 24.

According to FIG. 10, a deviation 54 between the circle 53 (or circle section 62) and the separation line 12 at least along the section 61 is calculated by integration of error squared.

This is done in a check step 55. The deviation 54 is compared to a deviation 56 which is obtained analogously according to FIG. 11 between the separation line 12 of the current image 9 and a circle 57, which is formed from a temporarily stored position indication 58 that corresponds to the position indication 23 for a preceding image 9 and a radius 59 that corresponds to a radius 51 relating to a preceding image 9.

If the deviation 54 is smaller than the deviation 56, the currently calculated position indication 23 and the currently calculated radius 51 are accepted and temporarily stored as position indication 58 and radius 59.

If the deviation 56 is smaller than the deviation 54, as is represented by way of example in FIGS. 10 and 11, the currently calculated position indication 23 and the currently calculated radius 51 are discarded, and the previously calculated values for the position indication 58 and the radius 59 are used or kept.

It is clear that the separation line 12 in a section 61 describes a circle section 62 of the circle 57, in this case even the full circle 57.

In an image editing step 60 of the image editing stage 22, the currently calculated values or the values kept from a preceding image 9 for the position indication 23 and the radius 51 are then used to enlarge the image content 10 or to scale and center it such that an image format provided by the image 9 is utilized if possible completely.

In the image processing method 18, in a completely computer-implemented and/or hardware-implemented statistical evaluation method 20, in each case a position indication 23 of a center 24 of the image content 10 of the individual images 9 is calculated for images 9 in an image sequence 8, wherein the center 24 is defined by a circle section 62 which is described or characterized by a separation line 12 between the image content 10 and a periphery 11 that is supplementary to the image content 10 in the image 9 or complementary therewith.

LIST OF REFERENCE SIGNS 1 endoscope arrangement
2 endoscope
3 image capturing device
4 proximal end
5 distal end
6 image processing apparatus
7 input
8 image sequence
9 image
10 image content
11 periphery
12 separation line
13 edge
14 means
15 FPGA (if appropriate with embedded microcontroller)
16 output
17 output unit
18 image processing method
19 preparation stage
20 statistical evaluation method
21 plausibility check stage
22 image editing stage
23 position indication
24 center
25 filtering step
26 image segmenting and histogram calculation step
27 image segment
28 line
29 intensity and/or color value histogram
30 threshold value
31 intermediate result
32 edge detection step
33 component ascertainment step
34 rows
35 intersection point
36 intersection point
37 horizontal component
38 column
39 intersection point
40 intersection point
41 vertical component
42 image content recognition step
43 second position indication
44 minimum extent
45 maximum extent
46 minimum extent
47 maximum extent
48 horizontal component
49 vertical component
50 radius ascertainment step
51 radius
52
53 circle
54 deviation
55 check step
56 deviation
57 circle
58 position indication
59 radius
60 image editing step
61 section
62 circle section

The invention claimed is:

1. An image processing method (18), comprising:
processing an image sequence (8) of images (9) which in each case have an image content (10) and a periphery (11) that is complementary to the image content (10),
separating the image content (10) from the periphery (11) by a separation line (12) that describes in at least a section (61) a circle section (62),
for each of the images (9) in the image sequence (8), ascertaining a position indication (23) of a center (24) of the image content (10) that is defined by the circle section (62) in at least one of a computer-implemented or hardware-implemented statistical evaluation method (20), and
carrying out at least one image editing step (60) for each said image (9) that processes at least the position indication (23) as a parameter, and centering the respective image content (10) in the image editing step (60).

2. The image processing method (18) as claimed in claim 1, further comprising in each case calculating a value for a component (37, 41) of the position indication for a selection of rows (34) or columns (38) from positions of intersection points (35, 36, 39, 40) of the row (34) or the column (38) with the separation line (12) in the statistical evaluation method (20).

3. The image processing method (18) as claimed in claim 2, further comprising selecting only the rows (34) or the columns (38) that are intersected by the circle section at two intersection points (35, 36, 39, 40).

4. The image processing method (18) as claimed in claim 2, further comprising calculating a frequency distribution of the values that are calculated for the selection of the rows (34) or the columns (38) in the statistical evaluation method (20).

5. The image processing method (18) as claimed in claim 4, further comprising for ascertaining the position indication (23), using the in each case most frequent calculated value for the selection of the rows (34) or the columns (38).

6. The image processing method (18) as claimed in claim 1, further comprising calculating at least one of an intensity or color value histogram (29) in at least one of computer-implemented or hardware-implemented fashion for the respective image (9) before the statistical evaluation method (20).

7. The image processing method (18) as claimed in claim 6, further comprising coloring all image pixels of the image (9), at least one of an intensity or color value of which lies under a threshold value (30), black.

8. The image processing method (18) as claimed in claim 7, wherein the threshold value (30) for an image segment (27) in which the respective image pixel is located, is individually prespecified or ascertained.

9. The image processing method (18) as claimed in claim 8, wherein the image segment (27) is defined by two lines (28) that cross in the image (9) or wherein the threshold value (30) is calculated from at least one of the intensity or color value histogram (29), or both.

10. The image processing method (18) as claimed in claim 1, further comprising applying an edge detection method (32) before the statistical evaluation method (20) for the respective image (9).

11. The image processing method (18) as claimed in claim 1, further comprising calculating a second position indication (43) for the center (24) as an average of a maximum extent (45, 47) and a minimum extent (44, 46) of the image content (10) in a row direction and in a column direction for each image (9), and the position indication (23) is discarded or the position indication (23) relating to a preceding image (9) in the image sequence (8) is kept if it deviates too strongly from the second position indication (43).

12. The image processing method (18) as claimed in claim 1, further comprising calculating a radius (51) of the circle section (62) for each of the images (9), with the radius (51) being calculated from a maximum extent (45, 47) and a minimum extent (44, 46) of the image content (10) in the row direction or in the column direction, or both.

13. The image processing method (18) as claimed in claim 12, further comprising calculating a deviation (56) of the separation line (12) from a circle (53) which is defined by the position indication (23) and the radius (51) along the section (61).

14. The image processing method (18) as claimed in claim 13, further comprising calculating a second deviation (56) of the separation line (12) from a circle (57) which is defined by the position indication (58) and the radius (59), which were calculated for a preceding image (9) in the image sequence (8), along the section (61), wherein the position indication (23) is discarded or the position indication (23) for a preceding image (9) in the image sequence (8) is kept if the deviation (54) is greater than the second deviation (56).

15. The image processing method (18) as claimed in claim 1, further comprising carrying out a further image editing step (60) for each of the images (9), with the further image editing step (60) including a matching of an enlargement such that the respective image content (10) fills an available image format.

16. An image processing apparatus (6), comprising:
an input (7), via which an image sequence (8) of images (9) having in each case an image content (10) and a periphery (11) that is complementary to the image content (10), wherein the image content (10) is separated from the periphery (11) by a separation line (12) which in at least a section (61) describes a circle section (62), is input,
an output (16) via which a position indication (23) of a center (24) of the image content (10) that is defined by the circle section (62) can be output for each image (9), and
a processing device (14) configured and adapted for carrying out an image processing method (18) as claimed in claim 1.

17. The image processing apparatus (6) as claimed in claim 16, wherein the processing device (14) are realized in an FPGA (15) and/or wherein an output unit (17) is adapted to output processed images.

18. An endoscope arrangement (1) having an endoscope (2), an image capturing device (3) connected to the endoscope to capture an image from a distal end of the endoscope, the image processing device signaling an input to an image processing apparatus (6) as claimed in claim 16.

* * * * *